(12) United States Patent  
Sukkau et al.

(10) Patent No.: US 12,144,664 B2
(45) Date of Patent: Nov. 19, 2024

(54) METHOD AND POSITIONING SYSTEM FOR DETERMINING A REGION TO BE EXAMINED IN A SUBJECT

(71) Applicant: Siemens Healthcare GmbH, Erlangen (DE)

(72) Inventors: Johann Sukkau, Herzogenaurach (DE); Helmut Wrobel, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 424 days.

(21) Appl. No.: 17/704,839

(22) Filed: Mar. 25, 2022

(65) Prior Publication Data

US 2022/0304634 A1 Sep. 29, 2022

(30) Foreign Application Priority Data

Mar. 26, 2021 (DE) ...................... 10 2021 202 978.7

(51) Int. Cl.
*A61B 6/04* (2006.01)
*A61B 6/03* (2006.01)

(52) U.S. Cl.
CPC ............ *A61B 6/0492* (2013.01); *A61B 6/032* (2013.01); *A61B 6/045* (2013.01)

(58) Field of Classification Search
CPC ........ A61B 6/045; A61B 6/032; A61B 6/0492
See application file for complete search history.

(56) References Cited

U.S. PATENT DOCUMENTS

| | | | |
|---|---|---|---|
| 10,393,829 | B2 | 8/2019 | Ludwig et al. |
| 2010/0052682 | A1 | 3/2010 | Mueller |
| 2013/0342851 | A1 | 12/2013 | Dresel et al. |
| 2016/0202864 | A1 | 7/2016 | Hardie et al. |
| 2016/0203265 | A1 | 7/2016 | Hardie et al. |
| 2016/0367169 | A1 | 12/2016 | Hardie et al. |

(Continued)

FOREIGN PATENT DOCUMENTS

| | | |
|---|---|---|
| DE | 102012209190 A1 | 12/2013 |
| DE | 102016203255 A1 | 8/2017 |

(Continued)

OTHER PUBLICATIONS

Sukkau, Johann; MRT-compatible hydraulic-electric linear drive; Siemens AG 2022.

*Primary Examiner* — Mark R Gaworecki
(74) *Attorney, Agent, or Firm* — Banner & Witcoff Ltd.

(57) ABSTRACT

A method and positioning system for determining a region to be examined in a subject on a movable support of a medical imaging system. The method includes: a) manually specifying the region by positioning a predetermined marker object in relation to the subject; b) acquiring the position of the marker object by an acquisition apparatus; c) projecting or displaying a feedback marking by a projection apparatus at the acquired position on the subject, wherein the position of the marker object and the acquired position are adjustable; d) calculating a scan position of the movable support on the basis of the acquired position by means of a computer unit, wherein in the scan position, the region to be examined is arranged in an acquisition region of the imaging system; and e) automatically moving the movable support into the scan position with a motor.

22 Claims, 2 Drawing Sheets

(56) References Cited

U.S. PATENT DOCUMENTS

| | | |
|---|---|---|
| 2017/0000446 A1 | 1/2017 | Brinker et al. |
| 2017/0209110 A1 | 7/2017 | Kiraly |
| 2018/0085025 A1 | 3/2018 | Ehrl et al. |
| 2018/0116518 A1 | 5/2018 | Rinck et al. |
| 2019/0012536 A1 | 1/2019 | Ferguson et al. |
| 2019/0027246 A1 | 1/2019 | Ferguson et al. |
| 2019/0029559 A1 | 1/2019 | Nufer et al. |
| 2022/0071564 A1 | 3/2022 | Sukkau et al. |

FOREIGN PATENT DOCUMENTS

| | | | |
|---|---|---|---|
| DE | 102020211327 A1 | 3/2022 | |
| WO | WO-2020254160 A1 * | 12/2020 | ........... A61B 6/0492 |

* cited by examiner

METHOD AND POSITIONING SYSTEM FOR DETERMINING A REGION TO BE EXAMINED IN A SUBJECT

TECHNICAL FIELD

The present disclosure relates to a method for determining a region to be examined in a subject, a method for determining a field of view for a scan, a method for training an artificial neural network for determining a field of view and a positioning system for determining a region to be examined in a subject.

BACKGROUND

An examination in a medical imaging system, for example, in the context of magnetic resonance tomography (MRT), computed tomography (CT) or MRT positron-emission tomography (MRT-PET) typically requires a medical technical assistant (MTA) position the patient on the patient support and then to ensure that the support is correctly positioned in the imaging system. For example, a laser beam can be directed at a fixed position on the patient, and the MTA moves the support manually to a position in which the laser beam points to the desired site on the patient. Once the desired site on the patient has been established, the support automatically moves with this site into the isocenter of the system. It is also known to communicate a support position and/or a site of the support to the system by numerical input. The isocenter is, in particular, the region in the imaging system that is best suited for an examination, for example, the region where the magnetic field of an MRT device is sufficiently homogeneous for imaging.

The previous approaches, however, require a certain amount of time, are often not intuitively usable and/or are sometimes very cumbersome. Sometimes, very heavy demands are made on the precision of the positioning, which in procedures known from the prior art cannot always be entirely met.

SUMMARY

It is therefore an object of the disclosure to provide a method and a system with which the positioning of a movable support with a subject lying thereon can be communicated to an imaging system quickly, easily and precisely.

According to a first aspect of the disclosure, a method for determining a region to be examined in a subject, in particular a patient, on a movable support of a medical imaging system, is provided. The method comprises the steps: a) manually specifying the region by positioning a predetermined marker object in relation to the subject; b) acquiring the position of the marker object by means of an acquisition apparatus; c) projecting and/or displaying a feedback marking by a projection apparatus at the currently acquired position on the subject and optionally adjusting the position of the marker object and the currently acquired position; d) calculating a scan position of the support on the basis of the acquired position by means of a computer unit, wherein in the scan position, the region to be examined is arranged in an acquisition region of the imaging system; e) automatically moving the support into the scan position with a motor. The disclosure can advantageously enable a region to be examined to be specified intuitively and with relatively little effort by the user. Therein, a particularly rapid and simultaneously exact positioning technique can be enabled. By way of the feedback marking, a feedback mechanism can further be enabled which can, on the one hand, enable a more reliable input and, on the other hand, can increase the trust of the user in this method. In particular, a medical workflow can thereby be particularly efficient and rapid.

The region to be examined can be, in particular, a site on the body of the patient. For example, the region to be examined can be a position in the longitudinal direction of the support. Thus, the region to be examined can be defined by a position on a one-dimensional scale. It is also conceivable that the region to be examined is defined in a two-dimensional plane, in particular, a plane parallel to the support, or that it is a three-dimensional region. In advantageous aspects, the region to be examined is determined through exactly one position and/or exactly one point, but can also have a one, two or three-dimensional extent. The region to be examined can be, in particular, a site on the surface of the subject, in particular on the body surface of the patient. It is alternatively also conceivable that, for example, by means of directional gestures, a region is identified which is situated within the subject, in particular, within the patient body. The region to be examined can be associated, for example, with a body part and/or an organ or can comprise the body part/the organ. During the method, it is preferably provided that the subject is situated lying on the support. Preferably, the subject therein moves as little as possible in relation to the support. The support can preferably be movable at least in its longitudinal direction. In particular, the support can be moved in and out of an examination region or a scan region of the imaging system. It is also conceivable that the support can also be movable in a direction perpendicularly to its longitudinal direction. In this regard and as described below, the longitudinal direction of the support can be designated the z-direction, a transverse direction of the support which is perpendicular to the z-direction and is substantially parallel to the support area, can be designated the x-direction and a direction perpendicular to the support surface as the y-direction. The medical imaging system can be, in principle, any imaging system which comprises a movable support and an, in particular stationary, examination region. Alternatively, the support can also be stationary and the imaging system can be movable in the z-direction. For example, the imaging system can be a magnetic resonance tomography (MRT) system, a computed tomography (CT) system or an MRT positron emission tomography (MRT-PET) system. The computer unit can be part of a control computer of the imaging system or a separate computer.

A manual input should be understood, in particular, to be input by a user or an operating person, for example, a medical technical assistant. The marker object can be, in principle, any object that is recognizable by the acquisition apparatus. In particular, the marker object can be a body part of the user or an object that is accessible to or movable by the user. In this context, predetermined preferably means that the marker object or its shape or appearance is stored in the acquisition apparatus or in a connected evaluating apparatus, so that, in particular, an image alignment between the marker object and a stored pattern can take place. The user can orient themself to the position of the subject and the region to be examined on the subject and can thus align the marker object directly in relation to the subject. This can enable, in particular, a direct and intuitive specification of the region. The acquisition of the position can mean, in particular, the acquisition of a predetermined portion of the marker object. For example, the tip of a rod or the outstretched fingertip of a user can be acquired. The position can be understood, in particular, to be a spatial coordinate. Alternatively or additionally, however, a spatial orientation of the marker object, for example, a rotary direction, can also fall under the definition of position.

With regard to the acquisition of the position, the marker object can be passive, active or independent. The acquisition apparatus which acquires the position of the marker object can itself be arranged on the marker object. For example, a position sensor and a transmitter apparatus can be arranged on the marker object (independent acquisition). Alternatively, the acquisition apparatus can also be arranged remotely from the marker object, for example, in the form of a camera which can acquire the marker object and a computer unit which can determine the position of the marker object from the camera image (passively). According to a further alternative, the acquisition apparatus can be arranged both partially on the marker object and also partially remotely from the marker object, for example, in the form of an infrared transmitter and receiver remote from the marker object and a retroreflector on the marker object. In principle, the combination of a plurality of (also different) acquisition apparatuses is also conceivable. This can enable, for example, a greater precision and/or a greater reliability to be achieved.

The projection and/or display of a feedback marking can enable the user, in particular, to recognize immediately whether the acquired position actually corresponds to the region envisaged by the user. In this regard, "at the currently acquired position" can mean, in particular, that the feedback marking is adjusted to a changing position of the marker object immediately or as quickly as possible. For example, it can be provided that, starting from the displayed feedback marking, the user adjusts the position of the marker object until the feedback marking is marked as precisely as possible or as necessary to the region to be examined. The feedback marking can preferably be a projected geometric form or a pattern which is suitable for displaying a position or a region. For example, the feedback marking can be a projected cross, a projected point, a 3D box or a suitably designed form. The system is configured to calculate a scan position by means of a computer unit. The scan position can preferably be a position of the support in which the region to be examined is or would be situated, in particular, in an acquisition region. For example, the scan position can be defined by means of the z-coordinate of the support. In addition, the scan position can optionally comprise the y-coordinates and/or the x-coordinates. The acquisition region can preferably be that region in which the imaging system, in particular, an imaging device or a scanner unit of the imaging system, can scan or can scan particularly well. For example, the acquisition region can correspond to the isocenter of the imaging system, can lie in the isocenter or can be arranged around the isocenter. For example, the imaging system can be configured to acquire the current position of the support automatically and, by comparison with the acquired position of the marker object, to ascertain how the support must be moved in order to bring the region to be examined into the acquisition region. The position of the support needed therefor can correspond, in particular, to the scan position. The system can then be configured, in particular, to move the support automatically into the scan position by means of a motor. The motor can be controlled, for example, by the computer unit or by a further computer unit of the imaging system. Preferably, the motor is a motor that is designed for operation in a magnetic field. Alternatively or additionally, it is conceivable that the motor is arranged externally, in particular, outside a scan region or the acquisition region. An interaction with the magnetic field of the imaging system can thereby be prevented or reduced.

According to one aspect, the feedback marking can be generated with a light source, in particular a laser, arranged over the support, wherein the light beam generated by the light source, in particular the laser, is incident at the acquired position at least substantially vertically on the object. This can be achieved, for example, in that the light source, in particular the laser, is movably arranged by means of a rail on the ceiling of the treatment room or on another fastening facility over the support. Preferably, the rail can extend along the longitudinal direction of the support or along the z-axis. In particular, the laser can be movable automatically by means of a motor along the rail parallel to the longitudinal direction of the support. Through a vertical incidence, a parallax error of the feedback marking can be reduced or prevented. A parallax error could cause the feedback marking to appear distorted or obliquely curved. Furthermore, in particular, if the height of the subject is not considered, the feedback marking could appear at a false position, in particular z-position. Substantially vertical means therein that smaller deviations, i.e. a slightly oblique position, e.g. ±10°, preferably ±5°, more preferably ±1°, could possibly still be acceptable in the context of this aspect. In particular, it can be provided, for example, that the direction of the incident light beam, in particular laser beam, has substantially no z-component, but a small x-component. This means that it can be provided that the light beam, in particular, the laser beam is incident substantially perpendicularly with regard to the longitudinal direction of the support, but with regard to the transverse direction of the support, has a deflection corresponding to the width of the support and the height of the mounted light source, in particular the mounted laser.

According to one aspect, it can be provided that the feedback marking is generated with a light source arranged over the support, in particular a laser, wherein the light beam, in particular the laser beam, is diverted with mirrors such that the light beam, in particular the laser beam, is incident at the acquired position at least substantially vertically on the object. The light source, in particular the laser, can therein be arranged at a fixed position in the z-direction, preferably centrally over the support. Through the diversion with mirrors, a substantially vertical incidence can be enabled in the entire longitudinal extent of the support without the light source itself, in particular the laser, needing to be moved in the z-direction.

According to one aspect, it can be provided that the light source, in particular the laser, generates a light beam, in particular a laser beam, with a beam direction lying in a horizontal plane, wherein the light beam generated, in particular the laser beam, is incident upon a parabolic mirror, in particular a flat parabolic mirror, wherein the focal point of the parabolic mirror coincides with the position of the light source, in particular the laser, so that the light beam, in particular the laser beam, is reflected a first time in the horizontal plane and perpendicularly to the longitudinal direction of the support, wherein the light beam, in particular the laser beam, is reflected a second time by a flat mirror arranged in the horizontal plane in front of the parabolic mirror such that it is deflected vertically in the direction of the support. A horizontal plane is, in particular, a plane which extends in the (x,z)-direction or extends substantially parallel to the support surface of the support. Through the placement of the light source or the laser in the focal point of the parabolic mirror, all the light beams or laser beams emerging from the light source or the laser are reflected parallel to the central axis of the parabolic mirror. In other words, it can be ensured that all the light or laser beams reflected by the parabolic mirror extend substantially parallel to the x-axis and substantially perpendicularly to the y-axis and the z-axis. The parabolic mirror can be defined, in particular, by a parabolic formula where $$x = a \times z^2$$

and the focal length $$f = \frac{1}{4 \times a}$$

For example, the parameter a can have a value of 15 cm$^{-1}$ to 35 cm$^{-1}$, preferably 20 cm$^{-1}$ to 30 cm$^{-1}$, and the support can have a length of 1.60 m to 2.50 m, preferably 1.80 m to 2.20 m. In particular, for a parameter value a of 25 cm$^{-1}$ and a length of the support of 2 m, the focus point can be provided at a distance of $$f = \frac{1}{4 \times 0.25 \text{ m}^{-1}} = 1 \text{ m}$$

from the apex of the parabolic mirror. A flat parabolic mirror can have the advantage that it can be produced more cheaply and/or more easily than a mirror curved in two directions. In addition, with a flat parabolic mirror, space over the support can be saved. The parabolic shape of the flat parabolic mirror is preferably arranged parallel to the horizontal plane, while the mirror is planar in the vertical direction. The flat parabolic mirror can be held, for example, by a frame, in particular, a frame the extension direction of which lies substantially in the horizontal plane, wherein the frame has only a small extent, in particular, in a direction perpendicular to the horizontal plane, in particular, an extent of the order of magnitude of the corresponding extent of the flat parabolic mirror. For example, it can be provided that the frame extends in the y-direction approximately at least exactly as far as, and not more than 20% further than, the parabolic mirror. Advantageously, an element generating a light pattern can be arranged between the light source or the laser and the parabolic mirror, in particular directly in front of the laser, wherein the element generating the light pattern is configured, in particular, to generate the form of the feedback marking from the light or laser beam. For example, the element generating the light pattern can be a diffractive optical element (DOE). A DOE is, in particular, an optical grating at which the laser beam is diffracted, for example, a glass substrate with a photolithographically applied microstructure, so that the laser beam is given the shape of the feedback marking. For example, by means of the DOE, both a pattern and also a beam divergence can be set. It can be provided to emit the laser beams emerging from the laser slightly tilted in the y-direction, for example, by an angle of 1°-10°, preferably 1°-5°. The parabolic mirror and/or the flat mirror can be fastened, for example, on the ceiling. Alternatively or additionally, the parabolic mirror and/or the flat mirror can be fastened to a fastening means, for example, a frame or a gantry, over the support. For example, the flat mirror can be arranged directly above or below the light source or the laser. It is also conceivable that the flat mirror is arranged, in relation to the parabolic mirror, directly behind the light source or the laser and nevertheless extends in the vertical direction or the y-direction above and/or below the light source or the laser than the light source or the laser. Alternatively or additionally, it can also be provided that the flat mirror is a semi-transparent mirror, wherein the flat mirror is arranged, relative to the parabolic mirror, in front of the light source or the laser. It can be provided, in particular, to generate the incidence point of the feedback marking in the z-direction such that the light source, in particular, the laser or the beam direction of the light beam emitted by the light source, in particular, the light beam emitted by the laser is rotated, in particular automatically, about a vertical axis or about the y-axis.

In particular, it can be provided that the position of the feedback marking is adjusted in the longitudinal direction of the support in that the light source, in particular the laser is rotated in the horizontal plane by means of a first motor controlled by the computer unit. Preferably, the first motor can be a motor that is designed for operation in a magnetic field. For example, an ultrasonic motor, an MR compatible stepper and/or servo motor, a pneumatic motor or a hybrid drive can be provided. In addition or alternatively, the position of the feedback marking can be adjusted in a transverse direction perpendicularly to the longitudinal direction of the support, in particular the x-direction, in that the flat mirror is rotated about itself by means of a second motor controlled by the computer unit about an axis parallel to the longitudinal direction of the support. Advantageously, the second motor can be selected according to the same aspects as the first motor. A deflection in the x-direction can be advantageous, in particular, in order to be able to specify or visualize an x-coordinate. For example, thereby a field of view, in particular of a first localizer can be visualized.

According to a further aspect, it can be provided that the feedback marking is generated with at least one light projection apparatus, in particular a video projector, arranged above the support and oriented toward the support, wherein the light projection apparatus comprises, in particular, a light source, a collimation optical system, an image formation unit and a projection optical system. The light source can be, for example, a laser, an LED and/or a lamp. A collimation optical system is, in particular, an apparatus which influences light beams such that they extend parallel. The image formation unit can be, in particular, statically (for example a diffractive optical element (DOE), slide or gobo), dynamic (for example a digital light processor (DLP) or liquid crystal on silicon (LCoS)) or dynamically transmissive (e.g. LCD). The image formation unit can serve, in particular, to shape or form the feedback marking as, for example, a cross. The projection optical system can comprise, in particular, mirrors or a mirror system for diverting the beams. The feedback marking is generated with at least one video projector arranged above the support and directed toward the support. The video projector can be configured, for example, to correct a parallax error digitally by adjusting the projected image. In addition or alternatively, it can be provided that the at least one video projector is movable on a longitudinal axis parallel to the longitudinal direction of the support. The video projector can be oriented, in particular, vertically or in the y-direction. For example, the video projector can be fastened on the ceiling or on a gantry or frame above the support. Advantageously, it can be provided to displace the video projector automatically for specifying the position of the feedback marking in the longitudinal direction of the support along the longitudinal axis of the support, in particular on a rail or linear axis. The displacement can be controlled, for example, by the computer unit or by a further computer unit and by means of a drive, in particular a motor, wherein the motor can be configured, in particular, to be operated in a magnetic field. It can also be provided to provide a plurality of projectors for generating the feedback marking. For example, it can be provided to use different colors for the feedback marking. Advantageously, the video projector can also enable complex patterns, in particular 3D images, to be generated. For example, it can be provided that by means of the video projector, a 3D image is projected, in particular, by means of augmented reality (AR)/HoloLens effect, onto the surface of the subject. The 3D image can be, for example, an FOV box which specifies a scan region, in particular for a first test scan or a localization scan. For example, it can also be provided to have the 3D image appear entirely or partially in the subject. For example, it can be provided that a user, in particular a medical technical assistant observes the 3D image with 3D glasses, in particular 3D shutter glasses or polarizing glasses. In addition, it can be provided that a surface, in particular, a blanket that is particularly suitable for the reproduction of the projection is arranged on the subject. For example, the surface can be chromatically uniform, in particular, white and/or can have a surface suitable for the projection of polarized light, in particular, an even smooth surface.

According to one aspect, it can also or alternatively be provided that the subject is monitored with a camera, in particular a 3D camera or a combination of a plurality of 2D and/or 3D cameras. The camera can be, for example, a 2D camera or a 3D camera. A combination of a plurality of 2D and/or 3D cameras is also conceivable. A 2D camera can, in particular, be relatively more economical and possibly have significantly higher resolution than a 3D camera. The 2D camera can be configured, in particular, to acquire the x and z-coordinates, for example of the fingertip. For example, the camera can be directed vertically downwards. A vertically downwardly directed 2D camera is, in particular, especially well suited to acquiring the x and z-coordinates. A 2D image can be ascertained, in particular, with known techniques of image processing. For example, two images can be recorded with the 2D camera, in particular, an image without the pointing hand and a further image with the hand. A difference between the two images can be used to obtain a mapping of the hand. Preferably, the hand of the user pointing to the patient can always be directed, seen from above, substantially along the x-axis, in particular, regardless of which table side the user is situated on. In this case, the fingertip can always be, in particular, the (X,Z)-point that is closer to the z-axis than all the other points of the difference image. A 3D camera can enable a recording in three spatial directions, in particular including the y-direction. A combination of a 3D camera and a high-resolution 2D camera can be particularly advantageous. It can be provided that the 3D camera is configured so that the presence of the pointing hand can be detected in 3D with the 3D camera and thereupon, the image recording and evaluation of the image differences with the 2D camera can be triggered. The y-coordinate of the fingertip can therein always be ascertained with the 3D camera. For example, the y-coordinate can have an accuracy of +/−(5−20) mm, preferably approximately +/−10 mm. The x and z-coordinates of the fingertip can be, particularly for position determination, more important than the y-coordinate. With the 2D camera, an accuracy of +/−(0.2−3) mm, preferably +/−1 mm can be capable of being ascertained for the (x,z)-coordinates. Advantageously, an accuracy of this type, in particular, in association with the optical feedback, can suffice to plan, for example, a surgical intervention. For example, the 3D camera can be used to carry out a parallax correction, in particular with the computer unit. In particular, it can be provided that, by means of the 3D camera, the height of the subject is determined at the acquired position, wherein by means of a computer unit, a parallax correction of the generated feedback marking is carried out. In particular, a correction of the feedback marking in the longitudinal direction of the support, in particular in the z-direction, and/or in a vertical direction, in particular in the y-direction, can be carried out. For example, it can be provided that the video projector is mounted and/or statically fixed at a site above the support, in particular is not movable in the longitudinal direction, and a parallax error on the basis of images of the subject and/or the support acquired by the 3D camera is corrected by the computer unit or a further computer unit. The 3D camera can be based, for example, on a stereoscopic acquisition, wherein the camera comprises, in particular, two lenses. Alternatively, the 3D camera can also be based on an encoding of a projected pattern wherein, on the basis of the distortion of the pattern on the acquired object, the three-dimensional topography of the acquired object can be determined. A time-of-flight-based 3D acquisition is also conceivable, wherein the camera comprises a projector which emits light, wherein on the basis of the time of flight of the reflected light, a three-dimensional position in space can be determined. Alternatively, a projection of stripes of differing width is conceivable, by means of which the three-dimensional position can be ascertained. Advantageously, the 3D camera can be firmly mounted or fixed statically above the support. Alternatively, it is also conceivable that the 3D camera is movable, for example, together or simultaneously with the video projector, on a rail, in particular in the longitudinal direction. Advantageously, a movement capability of the 3D camera can be used in order to acquire or to be able to acquire different views of the subject. For example, it can be provided that the 3D camera is moved on a linear axis, in particular parallel to the longitudinal direction of the support, wherein the camera records different views of the subject and assembles them into a 3D image, in particular a high-resolution 3D image. For example, it can be provided that the 3D camera carries out a movement over the subject and therein records images. Following the completed journey, the images can then be combined into an overall image. Through the movement of the 3D camera, it can advantageously be possible to reduce the spacing of the 3D camera and the support or the subject, in particular to 50 cm to 150 cm, preferably to 80 cm to 120 cm and particularly preferably to approximately 1 m, wherein nevertheless the whole region of the subject can be acquired. The region that can be acquired can typically be restricted by the angle of view of the camera or of the camera lens, so that by means of the region to be acquired, a minimum spacing from the subject can result, which is necessary in order to be able to acquire all the sites of the region. This restriction can advantageously be circumvented by a movable 3D camera. A camera placed closer to the subject can advantageously enable a higher image resolution of the overall image or a better effective spatial resolution. For example, image recordings by the 3D camera can be used to determine subject properties, in particular the size and/or weight and/or shape. Alternatively, by means of the image recordings, the position or surface coordinates of a local RF coil (radio-frequency coil for receiving the RF signal) can also be determined; this can be used in MRT-PET combination devices for calculating the attenuation correction, that is, the weakening of the PET image by the RF local coil. A higher effective resolution can enable a more exact determination of the parallax error and/or the position of the marker object. Advantageously, a drive or a drive motor can be selected for the movement of the 3D camera according to analog principles such as the motor for the laser or the mirrors.

According to one aspect which can be combined in particular with one of the other aspects, it can be provided that the marker object is a human hand, in particular a finger, of a user, wherein the position of the hand, in particular the finger, is ascertained by means of a camera, in particular a 3D camera. For example, it can be provided that a user, in particular a medical technical assistant, points with their hand toward a site in the subject, in particular, the body of the patient to be examined. The specification of the region with the hand or the finger can represent a relatively rapid and simple and also intuitive possibility for the position specification. For example, the position of the hand or the finger can take place with a camera, in particular a 3D camera, for example, with the 3D camera described above. The image data can be used in order to calculate a position, for example (x,y,z)-coordinates. In particular, a position of the fingertip can be ascertained automatically. The position can be ascertained either directly at the camera or the image data can be forwarded to a computer unit for ascertaining the position. It can be provided that the hand or finger is recognized as the lower end of a cylindrical object, in particular the arm of the user, with dimensions typical for the human anatomy or is stored as a recognition method in the computer unit. Furthermore, the approximate position of the arm and/or the hand can be stored, for example, as an approximately cylindrical object which extends from a point beyond the support, in particular from a shoulder obliquely from above to below in the direction of the support or the subject. With specifications of this type, a particularly reliable acquisition of the hand or the finger and thus a reliable determination of the position is enabled.

According to a further aspect, the marker object can be a hand-guided object, wherein the hand-guided object includes an active, passive or independent position sensor. For example, the hand-guided object can comprise an electronic system and/or sensor system for determining and/or specifying the position. The position can take place in particular on the basis of the location and/or orientation of the object in the room. Advantageously, the object can comprise an accelerometer and/or an inclinometer, in particular for determining an inclination of the object in order to acquire not only its position, but also its direction. For example, the object can also comprise a microcontroller for controlling, in particular in the case of an independent or active position sensor. The object can optionally comprise an on and off switch, in particular a button. A switch of this type can advantageously be suitable for saving energy. The object can be, for example, a rod ("a magic wand"). Advantageously, the inclination and/or direction of such a rod can be detected and thus the "position of the marker object" in this case can also be a position which is revealed in the extension of the rod, that is, a location to which the user points with the rod. A hand-guided object can enable an effective and intuitive specification of the position, wherein at the same time a relatively reliable position determination can be ensured.

In addition or alternatively to one of the other aspects, it can be provided that gestures with the hand, in particular the finger and/or the hand-guided object, are used as a position input for the input of a field of view of a scan to be performed with the imaging device and/or for communicating control commands, in particular with the aid of projected operating elements. For example, it can be provided that the outline of a field of view is drawn in the air. For example, it can be provided that the input of the field of view for specifying the field of view (FOV) of a first scan or test scan, in particular, a first localizer is used. In this way, it can be provided, in particular, to specify both the z-position or the position in the longitudinal direction of the support and also the x and y-positions or the spatial directions perpendicular to the longitudinal direction. The FOV can be defined, in particular, by means of vectors and/or scalars. For example, a vector (x, y, z) can be provided which gives the center of the FOV. This vector can be ascertained, in particular, from the acquired position. In addition or alternatively, it is conceivable that gestures on the basis of the temporal sequence of individual, in particular predetermined, positions are recognized, in particular acquired by the acquisition apparatus and evaluated by the computer unit or aligned with stored predetermined positions. For example, it can be provided that a movement of the marker object toward the subject and holding the position for a predetermined time, for example 1-2 seconds is acquired as position input. In particular, by way of the feedback marking, it can be ensured that the position input is correctly registered. Alternatively or additionally, on the one hand, a singular point can be specified as a position with the marker object, and also a region, for example, a circle, rectangle and/or polygon can be specified, in particular by circling the region. The region can define, in particular, the FOV. Alternatively or additionally, a movement of the marker object away from the subject, in particular in the direction of the acquisition region of the imaging system can be used as a command for moving the support into the acquisition region, wherein in particular, the acquired position is moved into an isocenter of the medical imaging system. The projected operating elements can be generated, for example, by way of a light projection apparatus, in particular a projector or video projector. For example, it can be provided with a projector to project buttons or operating elements, for example a green triangle, onto the support edge, particularly in reachable proximity of a user. In particular, a touch of the projected operating elements, in particular with the hand as a marker object, can be acquired by means of the acquisition apparatus. The touching of the operating elements can trigger, for example, an inward movement of the support or other commands. For example, in addition a touch display can be provided on which corresponding or the same operating elements can be displayed.

According to one aspect, the marker object can contain an active, passive or independent position sensor or position sensor element and, for specifying the region to be examined, can be placed on the desired region and fastened there on the subject. The marker object can comprise, for example, an energy store, in particular an accumulator or a battery for operating the position sensor, in particular in the case of an active and/or independent position sensor. In particular, it can be provided that a blanket, in particular a warming blanket will be or is placed on the subject, wherein the marker object is fastened on the blanket by means of an adhesive layer or by means of a hook and loop area. The marker object can be fastened, for example, by means of a hook and loop fastener on the subject and/or on the blanket lying on the subject. In particular, the blanket can comprise hook and loop areas. Alternatively or additionally, a fastening by means of hook and loop fastening can take place also on other objects which are arranged on the subject, for example, on hook and loop areas on flex coils. Alternatively or additionally, the marker object can comprise, for example, an adhesive layer for fastening. In particular, the blanket and/or other object can comprise a smooth layer for fastening the marker object to the adhesive layer. Alternatively or additionally, a fastening of the marker object can take place by means of belts. For example, the belts can be fastened form-fittingly and/or frictionally, in particular via a clip lock on the support. A placement of the marker object on the subject can enable an intuitive and comfortable specification of the position, wherein after the placement, the user can optionally attend to other tasks and/or a more thorough examination of the input position.

According to one aspect which, in particular, can be combined with the other aspects, the active, passive or independent position sensor can contain an illuminated optical retroreflector and/or an optical transmitter, wherein at least one 2D camera and/or 3D camera acquires the marker object or an ultrasonic or infrared transmitter, wherein the position of the position sensor is ascertained, in particular, by trilateration and/or triangulation or a magnetic field sensor, wherein the imaging device is a magnetic resonance device and the position is determined via the strength of the magnetic flux density at the magnetic sensor, wherein the strength of the magnetic flux density depends, in particular, on the spacing from the main magnet of the magnetic resonance device. In particular, the strength of the magnetic flux density can decrease with increasing distance from the main magnet. For example, 3 detectors which are configured to receive signals can be fastened on the room ceiling. An active position sensor can be, for example, an optical transmitter, in particular, one or more light-emitting diodes (LEDs), in particular infrared LEDs or an ultrasonic transmitter. The acquisition apparatus can be, in particular, a 2D camera or a 3D camera and/or an optical position sensor, for example, a position sensitive detector (PSD) sensor. In particular, three sensors can be provided wherein the sensors can be arranged in the corners of a triangle. Alternatively or additionally, a plurality of ultrasonic receivers can be provided which are configured, in particular, to calculate a position from ultrasonic signals received. The evaluation of the position can take place, in particular, by means of trilateration. Trilateration can mean, in particular, that the position is ascertained from a plurality of, in particular three, distance measurements. For example, a plurality of ultrasonic signals can be used for measuring a plurality of distances from reference points, wherein the position can be ascertained from the plurality of distances. Alternatively or additionally, the evaluation of the position can take place by means of triangulation. During the triangulation, for example, a distance between two base points can be known, wherein a triangle can be formed with a sought third position. If the angles between the distance between the base points and the respective distance from the base points to the position are now ascertained, the position can be ascertained therefrom. For example, the angles can be determined with at least one, preferably a plurality of 2D cameras or 3D cameras and with infrared rays. A passive position sensor element can be, for example, an optical retroreflector. A retroreflector is, in particular, an apparatus which reflects incident rays substantially independently of the angle of incidence and the alignment of the retroreflector substantially in the direction from which the rays come. In particular, a rod can be provided at its end with a plurality of glass spheres which are covered with silver. The glass spheres can each have, for example, a diameter of 20 to 200 micrometers, preferably from 40 to 160 micrometers and particularly preferably from 60 to 100 micrometers. The spheres can be arranged, for example, on a carrier at the end of the rod. For example, the carrier can also have a spherical form. For example, the retroreflector can contain a pattern, for example, a CR code. A pattern can be advantageous, in particular, if a plurality of marker objects is used, wherein a distinction of the different marker objects can be enabled. The medical imaging system can comprise an illumination apparatus with which the passive marker object can be illuminated, in particular with infrared radiation. Reflected rays can be acquired, for example, with at least one 2D camera and/or 3D camera. An independent position sensor can be configured, in particular, to ascertain the current position itself. The communication can take place by cable or wirelessly. In particular, the independent position sensor can comprise an ultrasonic transmitter and/or an optical transmitter, for example, an infrared link or a lightguide that is configured to communicate the position to the system. For example, the independent position sensor can comprise a 3D Hall probe which can ascertain a position on the basis of the outer magnetic field, in particular in the longitudinal direction of the support. A 3D Hall probe can be used, in particular in a medical imaging system which generates a magnetic field for scanning, for example, a magnetic resonance tomograph. In this case, the magnetic field can decrease with increasing distance outside the acquisition region, which can be used for position determination. In particular, a method or an apparatus as disclosed in the application DE 10 2016 203 255 A1 can be used. Alternatively or additionally, the position sensor can comprise an ultrasonic receiver, wherein a plurality of ultrasonic transmitters are arranged on the imaging system, for example, on a magnetic field-generating element or a magnet of the system. The position sensor can then receive ultrasonic signals of the ultrasonic transmitter and ascertain the position therefrom.

According to one aspect, it can be provided that an elongate depression is arranged laterally and in the longitudinal direction of the support and is provided with a touch sensor or distance sensor, in particular a laser sensor and/or an ultrasound sensor or with capacitive and/or resistive sensor strips for the measurement of a distance in the longitudinal direction representative for the position to be acquired, wherein the marker object is introduced for determining the position into the depression and is registered by the distance sensor. For example, the user can move the marker object, in particular their hand and/or a finger, into the lateral depression and thus interrupt or return a laser beam of the distance sensor or an ultrasonic wave or trigger the touch sensor. For example, laser sensors or ultrasonic distance sensors can be provided with a measuring range of up to a maximum of 2.2 m to 3 m, preferably up to 2.5 m and a resolution of 0.5 mm to 2 mm, in particular 1 mm. These values have proved to be a good compromise in practice, which relates both to a sufficient resolution and also technical practicability and incurred costs. From a measurement of the distance from a reference position, the position in the longitudinal direction or z-direction can be ascertained. On the basis of the feedback marking, the user can make fine adjustments to the position of the marker object if the acquired position is not yet exactly the intended position. The capacitive and/or resistive sensor strips can be arranged, in particular, along the depression. By means of the sensor strips, the position in the longitudinal direction can be, in particular, acquired electrically. An acquisition in the depression can represent a solution that is particularly economical and/or easy to implement, since the depression protects the distance or touch sensor against accidental triggering.

According to a further aspect, the subject and the support can be acquired and recorded with a 2D and/or 3D camera and displayed in a virtual environment, in particular, on a touch display, wherein the marker object is a finger, wherein the finger indicates the region to be examined in the virtual environment. This aspect can advantageously be implemented particularly well in existing systems since a touch display is often already present there. The image recording of the subject can take place, in particular, with an RGB sensor of the camera. In addition to the input of a position, a range, in particular a scan region can be specified, for example, by circling with the finger. After the input of the position, it can be provided that the user inputs a command for moving the support into the acquisition region, for example, on the touch display. According to one aspect, it can be provided that initially a general view of the subject is displayed, wherein after a first input by the finger, the environment around the currently acquired position is displayed in an enlarged representation, wherein the feedback marking is displayed both on the subject and also in the virtual environment, in particular on the touch display, wherein the user tests the position of the feedback marking and, if necessary, corrects it by means of a second input with the finger in the enlarged representation in order to specify more exactly the region to be examined. In particular, it can be provided that initially an image of the overall subject is displayed on the touch display and that after touching the touch display for position input of the image portion at the touched site or around the touched site, is enlarged. In the enlarged image portion, a more exact position input or position correction can then take place. It can be provided that a specified scan region on the touch display, in particular in the vertical direction and/or the y-direction, can be displaced manually. For example, it can be provided that a scan region is pushed into the subject. Alternatively or additionally, it is conceivable that the scan region can also be corrected or finely adjusted after the movement of the support into the scan region or into the isocenter. For example, it can be provided that after the determination of the scan region or the FOV, the center of a localizer, in particular a first localizer, coincides with the center of the FOV. For example, it can be provided that three standard slices, in particular, a sagittal, a coronal and a transversal plane are automatically scanned as soon as the support is at the determined position in the acquisition region.

According to one aspect, it can be provided that a field of view for a scan by the imaging system is determined on the basis of the position of the marker object and an offset in a sectional plane perpendicular to the longitudinal direction of the support, wherein the offset is determined on the basis of the body region of the subject associated with the respective region, in particular via empirical values of the offset and the size of the field of view. Empirical values can be based, for example, on recordings of previous scans and/or suitable tables. The field of view (FOV) can be used, in particular, to carry out a first localizer or a first test scan. The first localizer can comprise, in particular, a scan of the sagittal, coronal and transverse slices which intersect at the position of the marker object corrected by the offset. Advantageously, a medical workflow can thereby possibly be accelerated since a manual input of the localizer is no longer necessary and/or since the position of the localizer matches more exactly with the position of the organ to be examined. In particular, rather than extending through the isocenter, sagittal and coronal slices can extend through the position specified with the marker object (possibly including an offset). The FOV can be defined, in particular, by means of vectors and/or scalars. For example, a vector (x, y, z) can be provided which indicates the center of the FOV. This vector can be ascertained, in particular, from the acquired position. In order to specify the FOV more exactly, in particular within the subject, at least one offset from the position can be calculated. In particular, the offset can consist of two offsets in the spatial directions (x, y) perpendicularly to the longitudinal direction of the support (z-direction). Thereby, in particular, the position can be displaced into the subject, in particular vertically downwards and/or in the direction of the center of gravity in the (x, y) plane. The FOV position can be made up of the acquired position of the marker object MP and the two offset directions $MP_{offsetX}$ and $MP_{offsetY}$ as follows:

$$FOV\text{-Position}=MP+MP_{offsetX}+MP_{offsetY}$$

where $$MP_{offsetX}=(1,0,0)\times RegionFactorX(MP)$$

$$MP_{offsetY}=(0,-1,0)\times RegionFactorY(MP)$$

For example, an FOV normal can be a vector of length one or can be the value one, for example, defined in the transversal direction or the normal (0,0,1). In addition, an FOV rotation angle can be used, in particular, a scalar which gives the rotation, for example this value can be set to 0. Optionally, a size of the FOV, FOV-Größe(MP), can be taken from a table with predetermined values dependent on the respective position of the marker object (MP). The tables can contain, in particular, predetermined values for Region-FaktorX(MP), RegionFaktorY(MP) and FOV-Größe(MP), each dependent on the acquired position of the marker object MP. These values can depend on which region of the subject, in particular which body region of the patient, is selected or acquired. For example, a position on the abdomen according to the empirical values can require a deeper-lying and larger-dimensioned FOV than a position in or on the shoulder.

According to a further aspect of the disclosure, a method is provided for determining a field of view for a scan by the imaging system on the basis of a position of a marker object which marks a region to be examined in a subject, wherein the position has been determined, in particular, according to one of the preceding examples, wherein the determination of the field of view is carried out by an artificial neural network, wherein the neural network comprises an input layer for the input of input data which comprises the position of the marker object and optionally a size, a weight, a sex and/or a positioning, in particular the position and direction, of the subject, wherein the neural network comprises a plurality of covered layers, in particular 5 to 10 covered layers, wherein the neural network comprises an output layer which outputs at least the offset and the size of the field of view. All the features and advantages of the method for determining a region to be examined can be transferred similarly to the method for determining a field of view and vice versa. In particular, the aspects for determining the FOV, in particular, in relation to the offset can be used. Advantageously, tables of empirical values can be used or implemented as the basis or training data for the neural network. Advantageously, the neural network contains fully connected layers. The neural network can comprise, for example, 5 to 50 neurons, preferably 8 to 20 neurons in the input layer. Input values can be, for example, a patient height (in particular a value), a patient weight (in particular a value), a patient sex (in particular a value) a positioning (in particular 2 values, specifically a position and a direction), a body region to be examined (in particular as a numerically encoded value) and/or the position of the marker object (in particular 3 values, specifically the three spatial directions). With regard to the body region to be examined, for example, a predetermined numbering system can be provided, wherein a number is assigned to each of the body regions that are to be examined which are possibly examined in the known manner. This assigned number can then be, in particular, an input parameter. For example, the numbering can be 1=head, 2=heart, 3=knee, 4=left breast, 5=right breast, etc. In particular, the input values can be the parameters necessary for a scan. The parameters necessary for a scan can be designated scan protocols, in particular, in the case of an SHS-MR scan. Furthermore 2 to 30, preferably 5 to 10 covered layers can be provided which preferably each comprise 150 to 1300 neurons. The output layer can comprise, in particular, 2 to 30 neurons, preferably 5 to 10 neurons. Output values can comprise, in particular, the RegionFaktorX, the RegionFaktorY, the FOV-GrößeX, the FOV-GrößeY and the FOV-GrößeZ. By way of the use of a neural network, a particularly exact input or ascertainment of the FOV, in particular the first localizer, can be enabled. The numerical values specified with regard to the number of the layers and neurons can enable a particularly good compromise between computation effort and accuracy and reliability.

According to a further aspect of the disclosure, a method is provided for training an artificial neural network for determining a field of view for a scan by the imaging system on the basis of a position of a marker object which marks a region to be examined in a subject, wherein the position has been determined, in particular, according to example 20, wherein the neural network comprises an input layer, in particular comprising 8 to 20 neurons, a plurality, in particular 5 to 10 covered layers, in particular each with 150 to 1300 neurons, and an output layer, in particular with 5 to 10 neurons, wherein during the training, dropout layers are used, in particular with a dropout rate of 3-5%, wherein the method comprises the following steps: (1) providing input training data, wherein the input training data comprises the position of the marker object and, in particular, a height, a weight, a sex and/or a positioning, in particular, a position and direction, of the subject; (2) providing output training data which comprises data of an offset from the position of the marker object and a size of the field of view specified manually by a user from the input training data; (3) training the neural network with the input training data and the output training data, in particular by means of back propagation; (4) output of the trained neural network. All the features and advantages of the method for determining a region to be examined and the method for determining a field of view can be transferred similarly to the method for training an artificial neural network and vice versa. In particular, a feedforward network with back propagation can be used as a monitored learning method. The network can have a structure which corresponds substantially to the above described neural network. For example, one or more dropout layers can be provided with a dropout rate of 1% to 10%, preferably 3% to 5%. Training data can be, in particular, collected data from localizer positions manually specified in previous scans.

According to a further aspect of the disclosure, a positioning system is provided for determining a region in a subject, in particular a patient, that is to be examined, on a movable support of a medical imaging system, comprising an acquisition apparatus for acquiring the position of a marker object in relation to the subject, a projection apparatus for projecting and/or displaying a feedback marking at the acquired position on the subject, a computer unit, wherein the computer unit is configured to ascertain a scan position of the support on the basis of the acquired position, and a motor, wherein the motor is configured to move the support, in particular, in the direction of its longitudinal direction, wherein the computer unit is configured to drive the motor and to initiate a movement of the support into the scan position. All the features and advantages of the method for determining a region to be examined, the method for determining a field of view and the method for training an artificial neural network can be transferred similarly to the positioning system and vice versa. Preferably, the positioning system can comprise means for carrying out the steps of the method as described above.

BRIEF DESCRIPTION OF THE DRAWINGS

Further advantages and features are described in the following description of preferred aspects of the subject matter according to the disclosure, making reference to the accompanying drawings. Individual features of the individual aspects can be combined with one another in the context of the disclosure. Components corresponding to one another are each provided with the same reference characters.

In the drawings.

DETAILED DESCRIPTION

Figure 1:
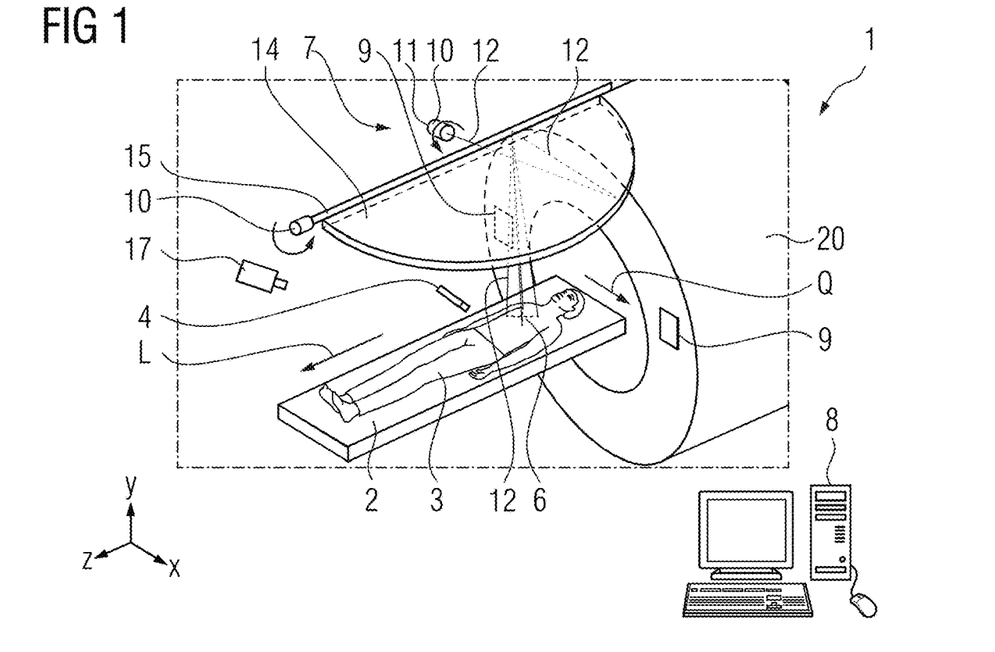
FIG. 1 shows a positioning system according to a first aspect.

FIG. 1 shows a positioning system according to a first aspect of the disclosure. The positioning system is, in particular, part of a medical imaging system 1 which in this case comprises a magnetic resonance tomograph (MRT) with an MRT tunnel 20. A subject 3, in particular a patient, can be placed for the purpose of an examination, on a support 2. In this case, the positioning system comprises a marker object 4 in the form of a rod which can be used to indicate the position of a region to be examined. The region can be acquired by means of a 3D camera 17 and calculated by the computer unit 8. In order to generate a feedback marking 6—in the form here of a cross—a projection apparatus 7 is used which herein comprises a laser 11 and a flat parabolic mirror 13 which is held by a frame 14. The flat parabolic mirror 13 is arranged such that the laser 11 or the location of the beam generation on the laser lies at its focal point. The laser is rotatable by means of a motor 10 in a horizontal plane which approximately corresponds to the plane of the frame 14. This is made clear by an arrow. A laser beam generated by the laser 11 is now incident at a site on the flat parabolic mirror 13 dependent on the rotation of the laser 11 and is reflected there. Therein, the reflected laser beam 12 is returned parallel to a transverse direction of the support 2 and is further reflected extending substantially in the horizontal plane, until it is incident upon a flat mirror 15. The flat mirror 15 then reflects the laser beam substantially perpendicularly downwardly in the direction of the support 2 or the subject 3. By means of a beam former directly in front of the laser 11, the laser beam is given a cruciate form which then appears on the subject as an illuminating cross 6. In this aspect, the flat mirror is also rotatable by means of a further motor 10 about an axis parallel to the longitudinal direction L of the support (indicated by an arrow). Through this rotation, a displacement of the feedback marking 6 can take place in a transverse direction Q of the support 2. Alternatively, the position can also be specified by means of a touch display 9 on which an image of the subject 3 recorded with the camera 17 can be displayed.

Figure 2:
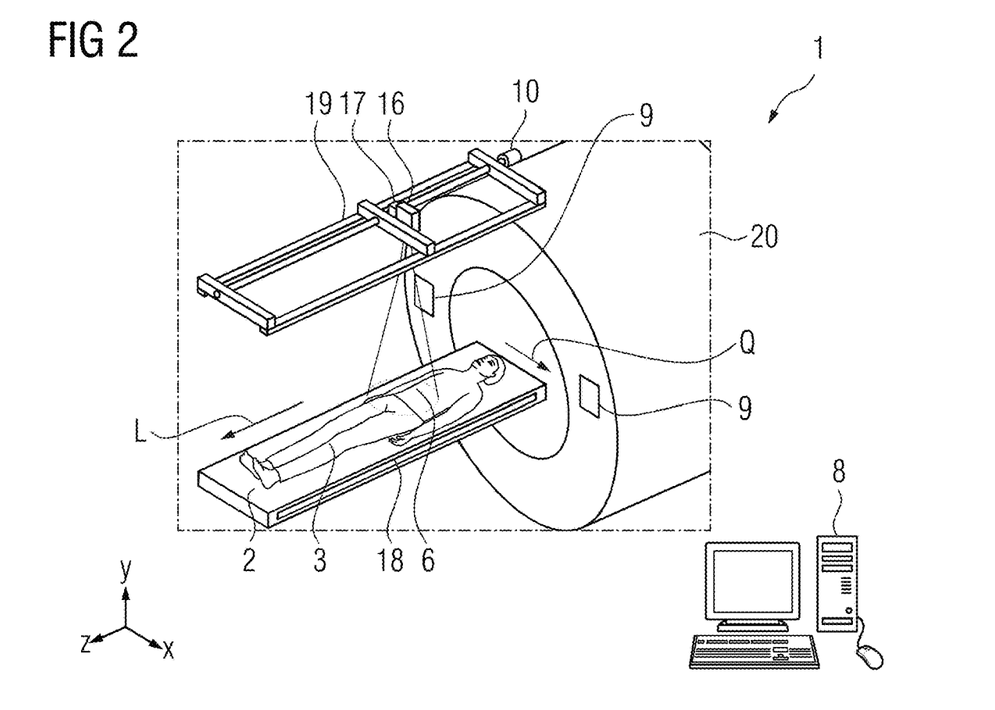
FIG. 2 shows a positioning system according to a second aspect.

FIG. 2 shows a positioning system according to a second aspect of the disclosure. This aspect differs from the first aspect, in particular, in that in this case the projection apparatus 7 is a video projector 16, which is movable on a linear guideway 19 in the longitudinal direction L. The feedback marking 6 can be generated on the subject 3 with the video projector 16. In addition to the video projector 16, a camera 17 is movable on the linear guideway 19. The movement takes place with the aid of a motor 10 and by means of a drive spindle mounted on the linear guideway 19 and/or by means of toothed belts (not shown) mounted on the linear guideway 19. The motor 10 can advantageously be an MR-compatible motor which is configured, in particular, to be operated in a magnetic field. For example, this can be a pneumatic motor, an ultrasonic motor or a hybrid drive.

According to a further aspect, an elongate depression 18 is arranged on the side of the support 2, in which the user can specify, by inserting a finger as the marker object 4, a z-position, which can be acquired by means of corresponding sensor systems. Additionally or alternatively, the position can also be specified directly on the subject 3 which can be acquired, in particular, by the camera 17.

Figure 3:
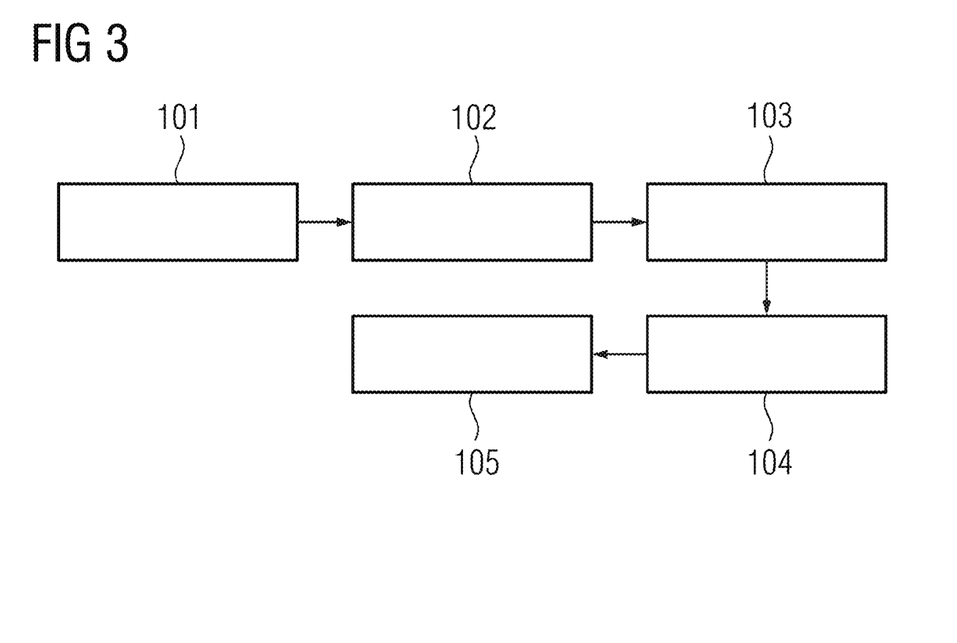
FIG. 3 shows a method according to one aspect of the disclosure.

FIG. 3 shows a method for determining a region to be examined in a subject 3. The subject 3 can be, in particular, a patient. In a first step 101, the region is specified by positioning a predetermined marker object 4 in relation to the subject 3 by a medical technical assistant (MTA). The marker object 4 can be, for example, a hand-guided object, for example, a rod or a marker which is placed on the subject 3 or is fastened on the subject 3. Alternatively, the marker object can also be the hand or finger of the MTA. The position of the marker object 4 is acquired in a next step 102 by an acquisition apparatus 5. The acquisition apparatus 5 can be, for example, at least one camera. The acquisition can however also be ultrasonically-based, wherein the acquisition apparatus 5 comprises one or more ultrasonic receivers. In a subsequent step 103, a feedback marking 6 on the subject 3 is indicated at the currently acquired position, in particular by projection. The indication or projection therein takes place with the aid of a projection apparatus 7. The projection apparatus 7 can comprise, in particular, a laser 11, the laser beam 12 of which is deflected with the aid of mirrors to the subject 3 or a video projector 16. In the following step 104, a computer unit 8 then calculates a scan position of the support 2 on the basis of the acquired position, so that in the scan position, the region to be examined is arranged in an acquisition region of the imaging system. Finally, in a last step 105, the support 2 is moved automatically into the scan position wherein the movement can take place, in particular, automatically with a motor.

Figure 4:
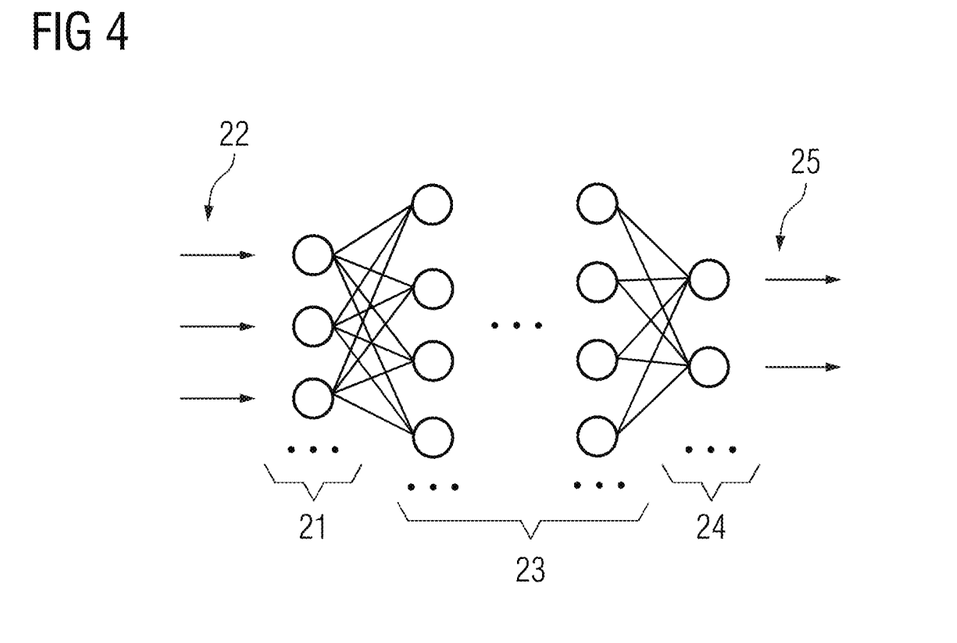
FIG. 4 shows a schematic representation of an exemplary neural network.

FIG. 4 shows a schematic representation of an exemplary neural network as can be used, in particular, for the method for determining a field of view (FOV). The neural network is not shown completely in this representation for reasons of clarity. It consists of an input layer 21. In this input layer, the input data 22 comprising the patient height, the patient weight, the patient sex, a positioning of the patient and the position of the region to be examined and optionally a number of the body region to be examined (for example 1=head, 2=heart, 3=knee, etc.). The neural network further comprises a plurality of covered layers 23 which also comprise some dropout layers with a dropout rate of between 3% and 5%. The output layer 24 supplies exclusively the output data 25 comprising offset factors for different spatial directions, in particular for the x-direction and y-direction and the size of the FOV in the three spatial directions. The different layers of the neural network are fully connected to one another. The neural network can preferably be trained with data used in previous scans.

The invention claimed is:

1. A method for determining a region to be examined in a subject on a movable support of a medical imaging system, the method comprising:
   a) manually specifying the region by positioning a predetermined marker object in relation to the subject;
   b) acquiring the position of the marker object by way of an acquisition apparatus;
   c) projecting or displaying a feedback marking by a projection apparatus at the acquired position on the subject, wherein the position of the marker object and the acquired position are adjustable;
   d) calculating, by a computer unit, a scan position of the movable support on the basis of the acquired position, wherein in the scan position, the region to be examined is arranged in an acquisition region of the medical imaging system; and
   e) automatically moving the movable support into the scan position with a motor.

2. The method of claim 1, wherein the feedback marking is generated with a laser arranged above the movable support, and a laser beam is diverted with mirrors such that the laser beam is incident at the acquired position at least substantially vertically on the marker object.

3. The method of claim 2, wherein the laser generates the laser beam with a beam direction lying in a horizontal plane, the laser beam generated is incident upon a flat parabolic mirror, a focal point of the flat parabolic mirror coincides with a position of the laser so that the laser beam is reflected a first time in the horizontal plane and perpendicularly to a longitudinal direction of the movable support, and the laser beam is reflected a second time by a flat mirror arranged in the horizontal plane in front of the flat parabolic mirror such that it is deflected vertically in the direction of the movable support.

4. The method of claim 1, wherein the feedback marking is generated with at least one video projector arranged above and oriented toward the movable support, and wherein a light projection apparatus comprises a light source, a collimation optical system, an image formation unit, and a projection optical system.

5. The method of claim 4, wherein the at least one video projector is movable on a longitudinal axis parallel to the longitudinal direction of the movable support.

6. The method of claim 1, wherein the subject is monitored with a 3D camera or a combination of a plurality of 2D and/or 3D cameras.

7. The method of claim 6, further comprising:
   determining, by means of the 3D camera, a height of the subject at the acquired position; and
   carrying out, by a computer unit, a parallax correction of the feedback marking generated.

8. The method of claim 6, further comprising:
   moving the camera on a linear axis parallel to a longitudinal direction of the movable support;
   recording, by the camera, different views of the subject; and
   assembling the different views into a 3D image.

9. The method of claim 1, wherein the marker object is a human finger, and a position of the human finger is ascertained by means of a 3D camera.

10. The method of claim 9, wherein gestures with the human finger are used as a position input for the input of a field of view of a scan to be performed with the 3D camera or for communicating control commands with the aid of projected operating elements.

11. The method of claim 1, wherein the marker object is a hand-guided object, which includes an active, passive, or independent position sensor.

12. The method of claim 11, wherein the active, passive, or independent position sensor comprises:
    an illuminated optical retroreflector or an optical transmitter, wherein at least one 2D camera or 3D camera acquires the marker object, or
    an ultrasonic or infrared transmitter, wherein a position of the position sensor is ascertained by trilateration or triangulation, or
    a magnetic field sensor and a magnetic resonance device, wherein the position is determined via a strength of magnetic flux density at the magnetic sensor, and the strength of the magnetic flux density depends on a spacing from the main magnet of the magnetic resonance device.

13. The method of claim 1, wherein the marker object comprises an active, passive or independent position sensor, and for specifying the region to be examined, is placed on a desired region and fastened there on the subject.

14. The method of claim 13, further comprising:
    placing a warming blanket on the subject; and
    fastening the marker object on the warming blanket by means of an adhesive layer or by means of a hook and loop area.

15. The method of claim 1, wherein an elongate depression is arranged laterally and in a longitudinal direction of the movable support and is provided with a touch sensor or distance sensor, a laser sensor, or an ultrasound sensor or with capacitive or resistive sensor strips for a measurement of a distance in a longitudinal direction representative for the position to be acquired, and wherein the marker object is introduced, for determining the position, into the depression and is registered by the distance sensor.

16. The method of claim 1, wherein the subject and the movable support are acquired and recorded with a 2D or 3D camera and displayed in a virtual environment on a touch display, and wherein the marker object is a finger, which indicates the region to be examined in the virtual environment.

17. The method of claim 16, further comprising:
    initially displaying a general view of the subject;
    displaying, after a first input by the finger, the environment around the acquired position in an enlarged representation, wherein the feedback marking is displayed both on the subject and also in the virtual environment on the touch display; and
    testing, by a user, the position of the feedback marking, wherein the position of the feedback marking is correctable by means of a second input with the finger in the enlarged representation in order to specify more exactly the region to be examined.

18. The method of claim 1,
    wherein a field of view for a scan by the medical imaging system is determined on the basis of the position of the marker object and an offset in a sectional plane perpendicular to the longitudinal direction of the movable support, and
    wherein the offset is determined on the basis of a body region of the subject associated with the respective region via empirical values of the offset and a size of the field of view.

19. A method for determining a field of view for a scan by the medical imaging system on the basis of a position of a marker object which marks a region to be examined in a subject, wherein the position has been determined by the method of claim 1,
    wherein the determination of the field of view is carried out by an artificial neural network, which comprises an input layer for an input of input data comprising the position of the marker object and a size, a weight, a sex, or a position and direction of the subject,
    wherein the neural network comprises 5 to 10 covered layers, and
    wherein the neural network comprises an output layer which outputs at least an offset and the size of the field of view.

20. A method for training an artificial neural network for determining a field of view for a scan by an imaging system on the basis of a position of a marker object which marks a region to be examined in a subject of claim 19,
    wherein the neural network comprises an input layer comprising 8 to 20 neurons, 5 to 10 covered layers each with 150 to 1300 neurons, and an output layer (24) with 5 to 10 neurons, wherein during the training, dropout layers with a dropout rate of 3-5% are used,
    wherein the method comprises:
    a) providing input training data that comprises the position of the marker object and a height, a weight, a sex, a body region to be examined, or a position and direction of the subject;
    b) providing output training data which comprises data of an offset from the position of the marker object and a size of the field of view specified manually by a user from the input training data;
    c) training the neural network with the input training data and the output training data by means of back propagation; and
    d) outputting the trained neural network.

21. A positioning system for determining a region to be examined in a subject on a movable support of a medical imaging system, comprising:
    an acquisition apparatus configured to acquire the position of a marker object in relation to the subject;
    a projection apparatus configured to project or display a feedback marking at the acquired position on the subject;
    a computer unit configured to ascertain a scan position of the movable support on the basis of the acquired position; and
    a motor configured to move the movable support in a direction of its longitudinal direction, wherein the computer unit is configured to drive the motor and to initiate a movement of the movable support into the scan position.

22. The positioning system of claim 21, comprising means for carrying out the steps of a method for determining a region to be examined in the subject on the movable support of the medical imaging system by:
    a) manually specifying the region by positioning the marker object in relation to the subject;
    b) acquiring the position of the marker object by way of the acquisition apparatus;
    c) projecting or displaying the feedback marking by way of the projection apparatus at the acquired position on the subject, wherein the position of the marker object and the acquired position are adjustable;

d) calculating, by the computer unit, a scan position of the movable support on the basis of the acquired position, wherein in the scan position, the region to be examined is arranged in an acquisition region of the imaging system; and e) automatically moving the movable support into the scan position with the motor.

* * * * *